United States Patent [19]

Carol

[11] Patent Number: 5,037,374
[45] Date of Patent: Aug. 6, 1991

[54] STEREOTACTIC-GUIDED RADIATION THERAPY SYSTEM WITH VARIABLE-LENGTH COMPENSATING COLLIMATOR

[76] Inventor: Mark P. Carol, R.D. 1, Box 122B, Milford, N.Y. 13807

[21] Appl. No.: 443,893

[22] Filed: Nov. 29, 1989

[51] Int. Cl.[5] ............................................. A61N 5/00
[52] U.S. Cl. ........................................ 600/1; 606/130; 378/65
[58] Field of Search .......................... 600/1; 606/130; 128/804; 378/64, 65, 159

[56] References Cited

U.S. PATENT DOCUMENTS

| | | | |
|---|---|---|---|
| 3,755,672 | 8/1973 | Edholm et al. | 378/158 |
| 4,172,979 | 10/1979 | Morrison | 378/65 |
| 4,583,537 | 4/1986 | Derechinsky et al. | 606/130 |
| 4,805,615 | 2/1989 | Carol | 128/303 |

OTHER PUBLICATIONS

Barish, R., Barish, S., "A New Stereotactic X-Ray Knife," Int. J. Radiation Ocology Biol. Phys., 14:1295–1298, 1988.
Columbo, F., et al., "External Stereotactic Irradiation by a Linear Accelerator", Neurosurgery, 16:160, 1985.
Hartmann, G., et al., "Cerebral Radiation Surgery Using Moving Field Irradiation at a Linear Accelerator Facility," Int. J. Radiation Ocology Biol. Phys. 11: 1185–1192, 1985.
Heifetz, M., et al., "Single–beam Radiotherapy Knife," J. Neurosurgery, 60:814–818, 1984.
Houdek, P., et al., "Stereotaxtic Radiotherapy Technique for Small Intracranial Leisions," Med. Phys., 12:469–472, 1985.
Leksell, D., "Stereotactic Radiosurgery: Present Status and Current Trends", Neurological Research, 9:60–68, 1987.
Leksell, L., "The Stereotactic Method and Radiosurgery of the Brain," Acta Chir. Scan., 102:316–319, 1951.
Lutz, W., et al., "A System for Stereotactic Radiosurgery with a Linear Accelerator," Int. J. Radiation Oncol. Biol. Phys., 12:373–381, 1988.
Pike, B., et al., "Dose Distributions in Dynamic Stereotactic Radiosurgery," Med. Phys., 14:780–789, 1987.
Podgorsak, E., et al., "Dynamic Stereotactic Radiosurgery," Int. J. Radiation Onc. Biol. Phys., 14:115–126, 1987.
Sturm, V., et al., "Stereotactic Percutaneous Single Dose Irradiation of Brain Metastasis with a Linear Accelerator," Int. J. Radiation Oncology Biol. Phys., 13:179–282, 1987.
Winston, K., et al., "Linear Accelerator as a Neurosurgical Tool for Stereotactic Radiosurgery," Neurosurgery, 22:454–464, 1986.

Primary Examiner—William E. Kamm
Assistant Examiner—Kevin Pontius
Attorney, Agent, or Firm—Ben D. Tobor

[57] ABSTRACT

A system for stereotactic-guided radiation therapy, method of stereotactic-guided radiation therapy, and a collimator useful in treating a patient with stereotactic-guided radiation therapy includes a variable length pathway for the beam of radiation, the pathway having associated therewith a material substantially equivalent to the tissue of the patient, whereby the radiation beam always travels through the same distance of actual tissue and tissue equivalent material.

24 Claims, 5 Drawing Sheets

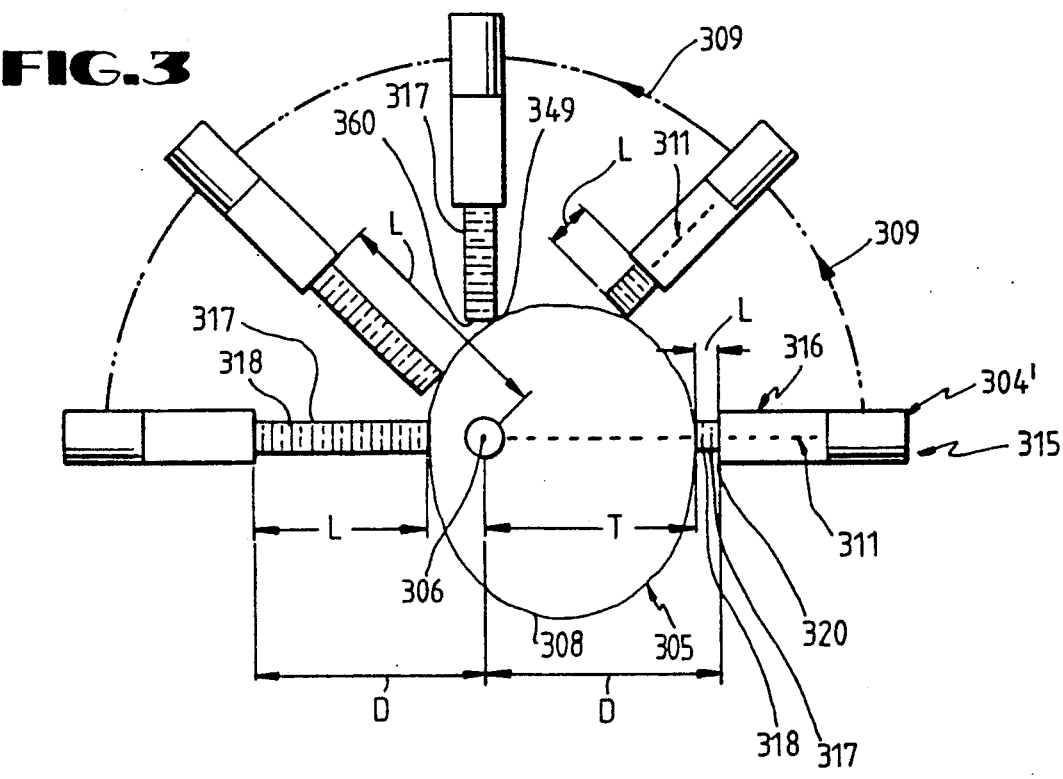
FIG.3
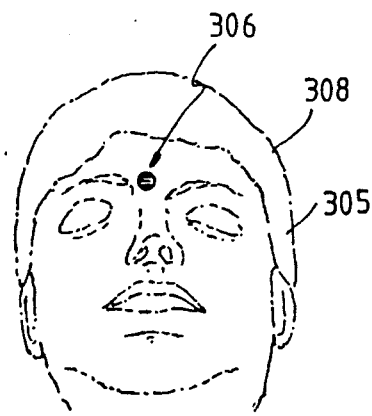
FIG.4
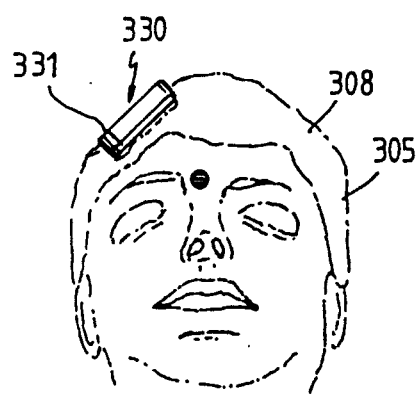
FIG.5
FIG.6

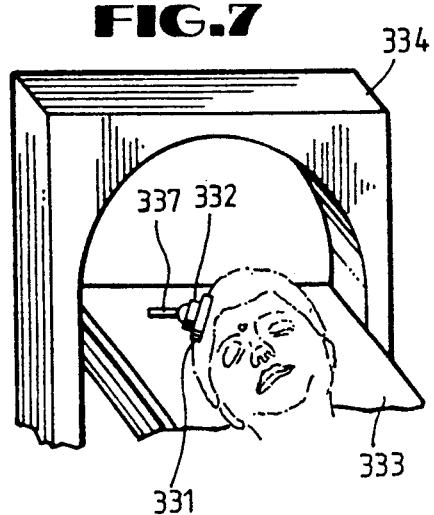
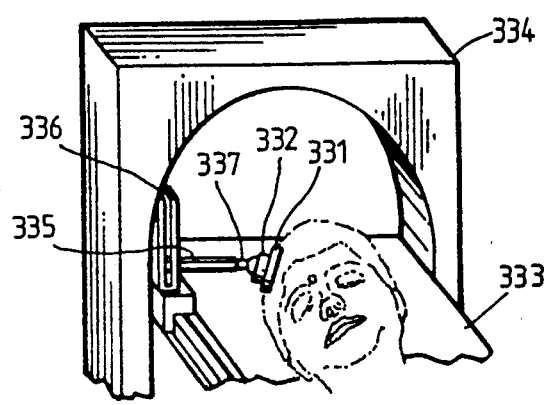
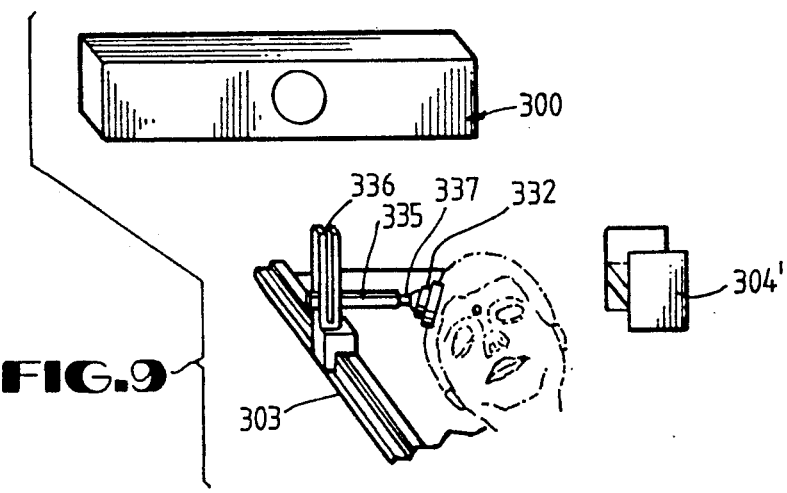
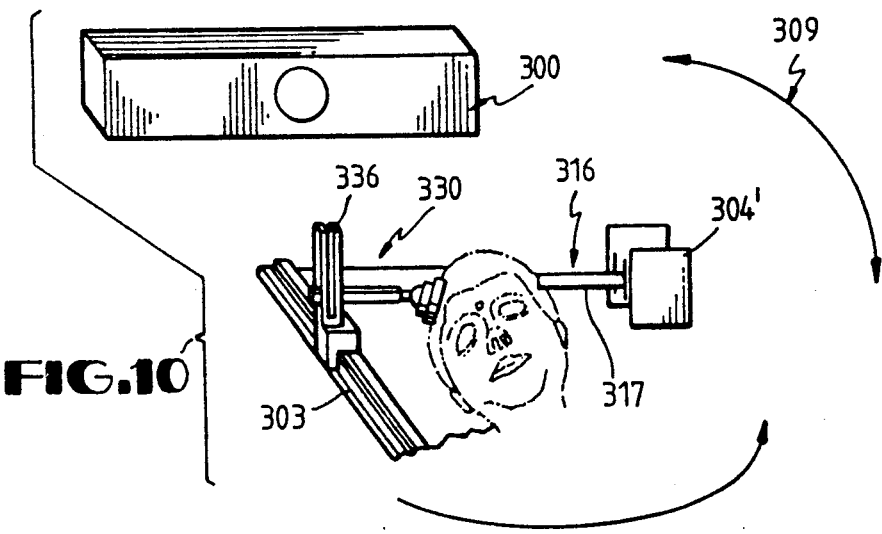

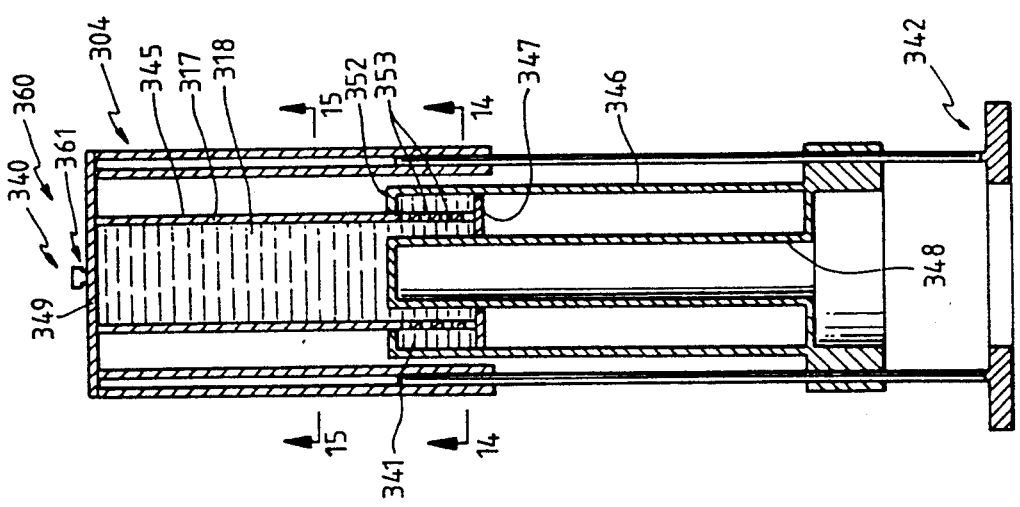
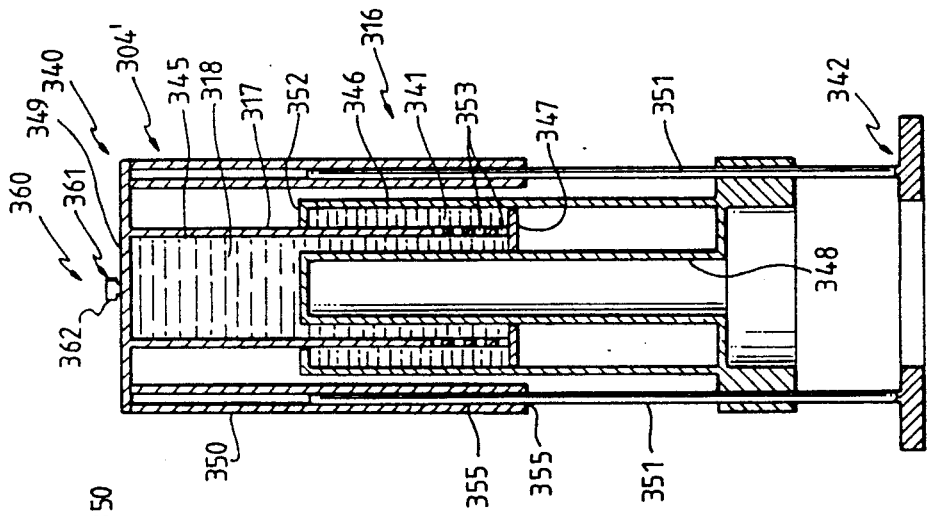
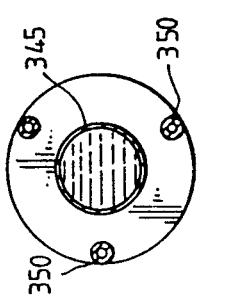
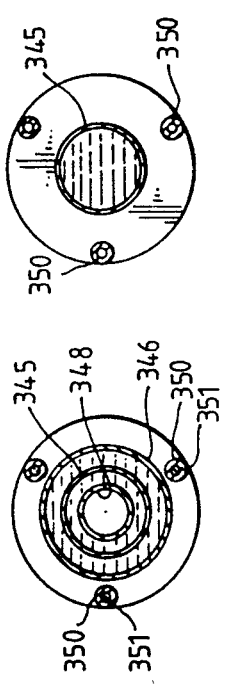
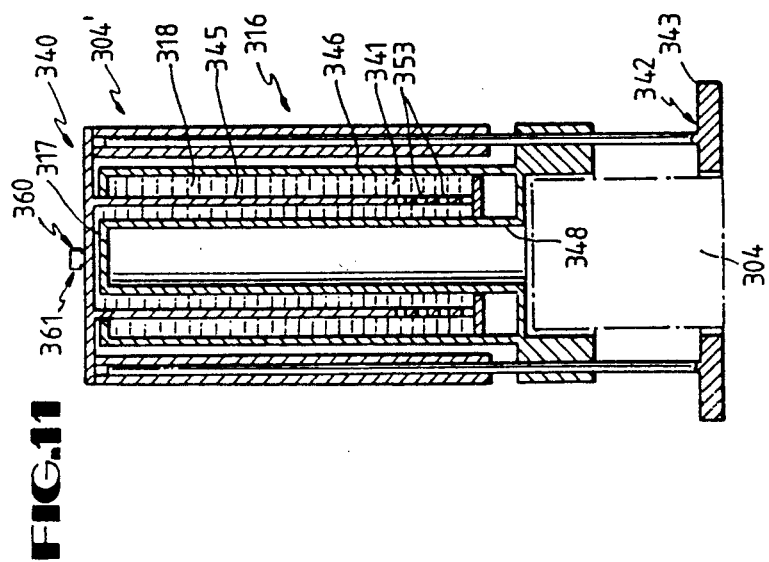

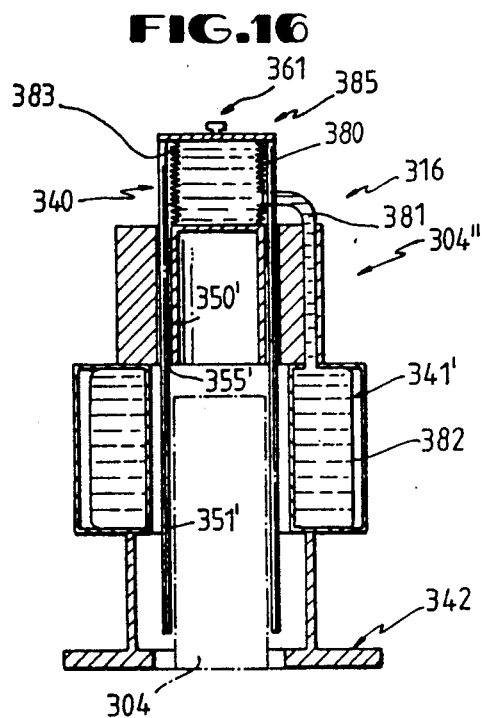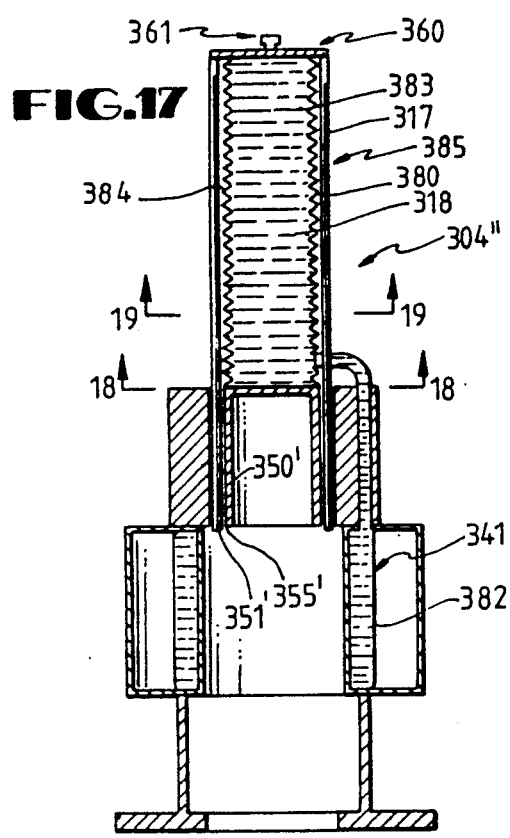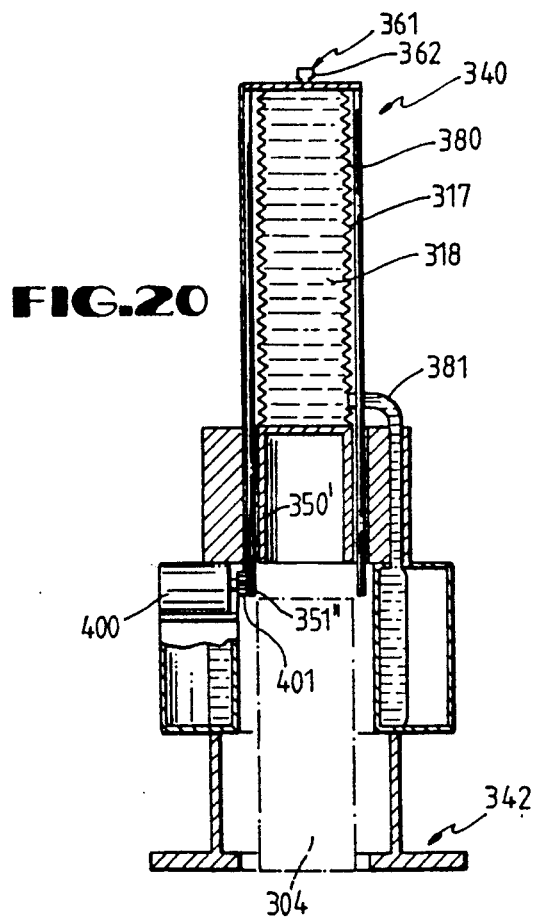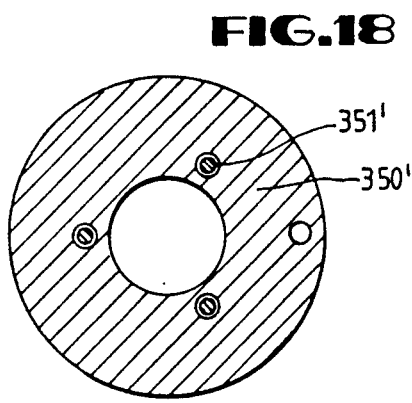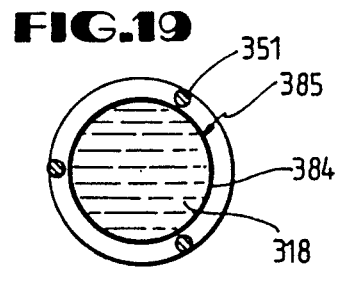

STEREOTACTIC-GUIDED RADIATION THERAPY SYSTEM WITH VARIABLE-LENGTH COMPENSATING COLLIMATOR

1. FIELD OF THE INVENTION

The invention relates to a stereotactic-guided radiation therapy system, a collimator useful in treating a patient with stereotactic-guided radiation therapy, and a method of stereotactic-guided radiation therapy of a lesion within a patient's body.

2. DESCRIPTION OF THE PRIOR ART

Dr. Lars Leksell in 1951 introduced radiosurgery, which used a Gamma Knife to deliver a high dose of ionizing radiation delivered to a pre-selected, stereotactically localized intracranial volume of normal or pathological tissue. Although success has been achieved by this technique in treating otherwise inaccessible abnormalities in the central nervous system, investigators have been looking at other means of accomplishing the same results. Although systems based on the beam characteristics of heavy charged particles have been in use for a number of years, the greatest amount of interest lies in applications involving linear accelerators, due to the fact that the cost of acquiring either a Gamma Knife, or a heavy particle system is significant, whereas many hospitals already possess linear accelerators.

The principle behind linear accelerator-based systems is that by rigidly fixating a patient to the accelerator rotatable couch so that the target, or lesion inside the patient's skull lies at the isocenter of the accelerator, the total radiation dose delivered to the tumor, lesion, or target, can be distributed over a large treatment vector by either simultaneously or independently rotating both the gantry of the linear accelerator and the couch. The tumor receives a large dose of radiation, while due to the steep dose dropoff, resulting from the large application vector, normal brain tissue is spared.

Linear accelerator systems, depending upon the technique employed, use either: a single plane of rotation of the isocentric mounted linear accelerator to deliver the total dose of radiation; multiple, non-parallel but converging arcs; or a dynamic mode of therapy where both the couch and the gantry rotate simultaneously. In single-plane systems, because all of the radiation is delivered in that single plane, conventional two-dimensional planning systems can be used to determine isodose curves. The dose fall-off outside the target volume in the plane of the treatment are not sharp enough compared to the Gamma Knife to warrant usage of this technique. Both of the other techniques, which distribute radiation over a much greater arc than does the single-plane method, produce isodose curves with drop-offs similar to that of the Gamma Knife. However, the treatment planning for such approaches requires three-dimensional algorithms for dose calculations. This necessity is based upon the fact that the treatment radiation beam passes through different thicknesses of tissue as it rotates around the head, or other portion of the patient's body. Thus the amount of radiation the target receives depends upon the precise path that the radiation beam follows.

In general, rotating arc protocols treat roughly spherical lesions centered near the isocenter of the system with the isodose distributions approximated by two-dimensional calculations dependent upon the depth of the target, lesion, or tumor. In order to predict precisely the isodose contours which will result from any given treatment protocol necessitates the use of sophisticated planning systems which have the capability to handle the three-dimensional calculations required on such applications; however, such systems are both computer hardware and software intensive and very expensive. The only time that such planning is not necessary is in the theoretical case where the skull is a perfect sphere and the target, or tumor, is at the exact center of that sphere. In this unique case, the target receives the same dosage of radiation regardless of radiation beam position, the isodose curves becoming standardized.

For stereotactic-guided radiation therapy, treatment plan verification is computer labor-intensive because it is a three-dimensional problem. The amount of radiation which any given area of the brain, or other portion of the body, will receive from the treatment radiation beam is dependent upon the amount of tissue through which the beam has to pass and is attenuated, or dissipated, on its way to that particular area of the brain, or other portion of the body. The computer must have stored the contour of the scalp, the location of the target, or tumor, and the position of the beam rotations. It then constructs a three-dimensional matrix, which sums the radiation to every point in the brain, or other portion of the body, receives from every position of the radiation beam for all the rotations added together. Finally, it must display the results as conventional isodose curves. If the dose distribution misses parts of the target, or if vital tissue structure receives too much of a dose of radiation, either the target location, the beam size, or the location of the rotations must be changed and a new plan verification performed. Accordingly, such process is expensive, time consuming, and requires sophisticated, expensive computers to perform the necessary calculations.

Accordingly, prior to the development of the present invention, there have been no stereotactic-guided radiation therapy systems, methods, and collimators which: are simple and economical to manufacture and use; do not require a sophisticated three-dimensional treatment planning system, including expensive computer hardware and software; permits the use of a hospital's existing linear accelerator without modification to the accelerator head of the linear accelerator; and permit the use of stereotactic-guided radiation therapy on lesions in other parts of the body other than the skull.

Therefore, the art has sought stereotactic-guided radiation therapy systems, methods and collimators, which: are simple and economical to manufacture and use; do not require a sophisticated, expensive three-dimensional treatment planning system, including expensive computer and sophisticated software; permit the use of a hospital's existing linear accelerator without modification of the accelerator head; and may be used to treat targets, or tumors, in other areas of the patient's body, other than the patient's skull.

SUMMARY OF THE INVENTION

In accordance with the invention, the foregoing advantages have been achieved through the present system for stereotactic-guided radiation therapy for treating a patient. The present invention includes: a stereotactic fixation device; a linear accelerator having a rotatable couch; and a collimator for focusing a beam of radiation from the linear accelerator, including means for providing a variable length pathway for the beam of radiation, the pathway having a material substantially equivalent to tissue of the patient associated with the pathway, the beam of radiation passing through the pathway prior to entering the patient. Another feature of the present invention is that the tissue equivalent material may be water.

Another feature of the present invention is that the variable length pathway providing means may include a variable length, movable housing which contains the tissue equivalent material. Another feature of the present invention is that the variable length pathway providing means may include a reservoir for the tissue equivalent material, and the variable length, movable housing may be a variable length, movable piston, and the piston contains the tissue equivalent material. An additional feature of the present invention is that the housing may have a first end, adapted to contact the patient, and means for controlling the movement of the housing, whereby the first end of the housing maintains contact with the patient. Another feature of the present invention is that the variable length, movable housing may be a variable length movable piston, and the piston contains the tissue equivalent material, the piston being a plastic encased spring, which forms a variable length, movable bellows for containing the tissue equivalent material.

In accordance with another aspect of the invention, the foregoing advantages have been achieved through the present method of stereotactic-guided radiation therapy of a lesion within a patient's body. This aspect of the present invention includes the steps of: placing the patient on a rotatable couch associated with a linear accelerator having a collimator and a gantry; disposing the lesion of the patient at the isocenter of the linear accelerator; focusing a beam of radiation toward the lesion and through a variable length pathway associated with the collimator, the pathway having a material substantially equivalent to the tissue of the patient, the beam of radiation passing through the pathway prior to entering the patient; moving the collimator with respect to the patient while focusing the beam of radiation toward the lesion; and varying the length of the variable length pathway while moving the collimator, so that the beam of radiation passes through substantially the same distance of tissue and tissue equivalent material while the collimator is being moved.

A feature of the present invention is the step of utilizing water as the tissue equivalent material. Another feature of the present invention is the step of contacting the patient with a first end of the variable length pathway and maintaining such contact while the collimator is being moved by varying the length of the variable length pathway. An additional feature of the present invention is the step of disposing a first end of the variable length pathway a predetermined distance from the patient, and maintaining the predetermined distance between the first end and the patient while the collimator is moving by varying the length of the variable length pathway.

In accordance with another aspect of the invention, the foregoing advantages have been achieved through the present collimator useful in treating a patient with stereotactic-guided radiation therapy. This aspect of the present invention includes: means for focusing a beam of radiation; and means for providing a variable length pathway for the beam of radiation, the pathway having a material substantially equivalent to tissue of the patient associated with the pathway, the beam of radiation passing through the pathway prior to entering the patient. Another feature of the present invention is that the tissue equivalent material may be water. An additional feature of the present invention is that the variable length pathway providing means may include a variable length, movable housing which contains the tissue equivalent material.

A further feature of the present invention is that the variable length pathway providing means may include a reservoir for the tissue equivalent material. Another feature of the present invention is that the variable length movable housing may be a variable length movable piston, and the piston contains the tissue equivalent material. The piston may be a plastic encased spring which forms a variable length, movable bellows for containing the tissue equivalent material. A further feature of the present invention is that housing may have a first end, adapted to contact the patient, and means for controlling the movement of the housing, whereby the first end of the housing maintains contact with the patient. Another feature of the present invention is that the control means may be a means for spring biasing the first end of the housing into contact with the patient.

The system for stereotactic-guided radiation therapy, method of stereotactic-guided radiation therapy, and collimator useful in treating a patient with stereotactic-guided radiation therapy, when compared with previously proposed prior art methods and apparatus, have the advantages of: being simple and economical to manufacture and use; do not require a sophisticated three-dimensional treatment planning system, including sophisticated computer hardware and software; permit the use of a hospital's existing linear accelerator, and do not require modification of the accelerator head; and may be used to treat targets, or tumors, in areas of other parts of the patient's body, other than the human skull.

BRIEF DESCRIPTION OF THE DRAWINGS

In the drawings:

FIG. 3 is a top, schematic view illustrating a patient's skull being treated in accordance with the present invention;

FIGS. 4–10 are perspective views of a human patient having a tumor in his skull being treated in accordance with the present invention;

FIGS. 11–13 are partial cross-sectional views of a collimator in accordance with the present invention;

FIG. 14 is a partial cross-sectional view of a collimator taken along line 14—14 of FIG. 13;

FIG. 15 is a partial cross-sectional view of a collimator in accordance with the present invention taken along lines 15—15 of FIG. 13;

FIGS. 16–17 and 20 are partial cross-sectional views of a collimator in accordance with the present invention;

FIG. 18 is a partial cross-sectional view of a collimator in accordance with the present invention, taken along line 18—18 of FIG. 17; and FIG. 19 is a partial cross-sectional view of a collimator in accordance with the present invention, taken along lines 19—19 of FIG. 17.

While the invention will be described in connection with the preferred embodiment, it will be understood that it is not intended to limit the invention to that embodiment. On the contrary, it is intended to cover all alternatives, modifications, and equivalents, as may included within the spirit and scope of the invention as defined by the appended claims.

DETAILED DESCRIPTION OF THE INVENTION

Figure 1:
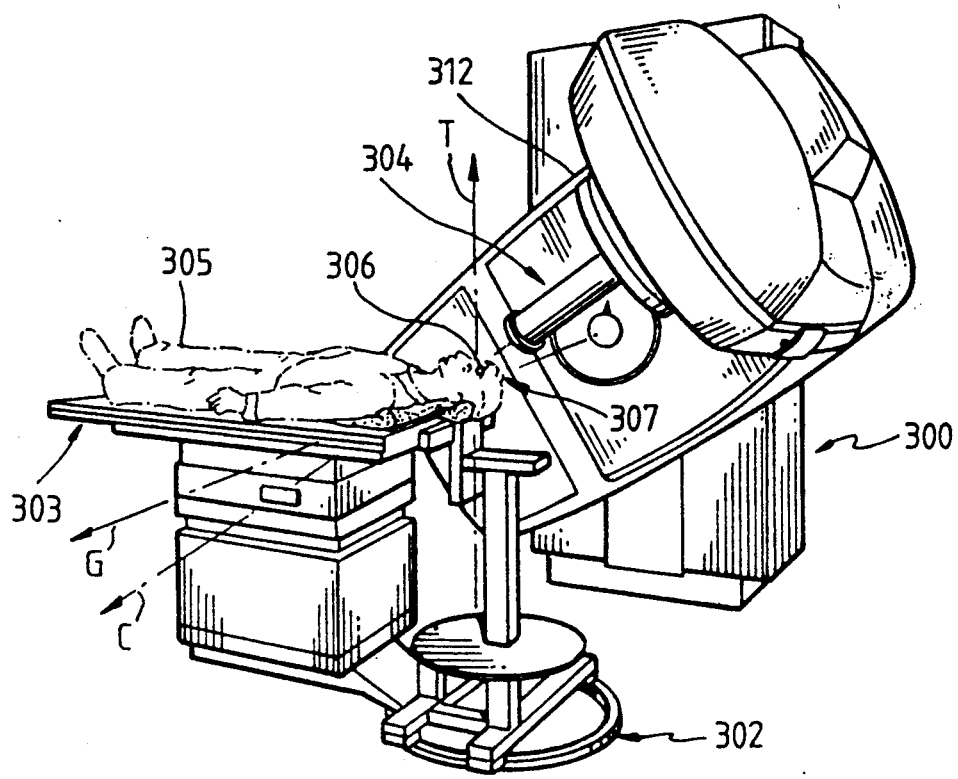
FIG. 1 is a perspective view of a conventional linear accelerator including a rotatable couch, collimator and gantry.

With reference to FIG. 1, a conventional linear accelerator 300 is shown as including a gantry 301, turntable 302 which causes patient couch 303 to rotate therewith, and a conventional collimator 304. The three axes of rotation of the gantry 301, turntable and couch 302, 303, and collimator 304 are designated with the letters G, T, and C, respectively. As illustrated in FIG. 1, the patient 305 is disposed upon the rotatable couch 303 by use of a conventional stereotactic fixation device (not shown) whereby the target, lesion, or tumor, 306 is disposed at the isocenter 307 of the linear accelerator 300. The isocenter 307 is defined as the point of intersection of the three axes of rotation, C, G, and T of linear accelerator 300.

Figure 2:
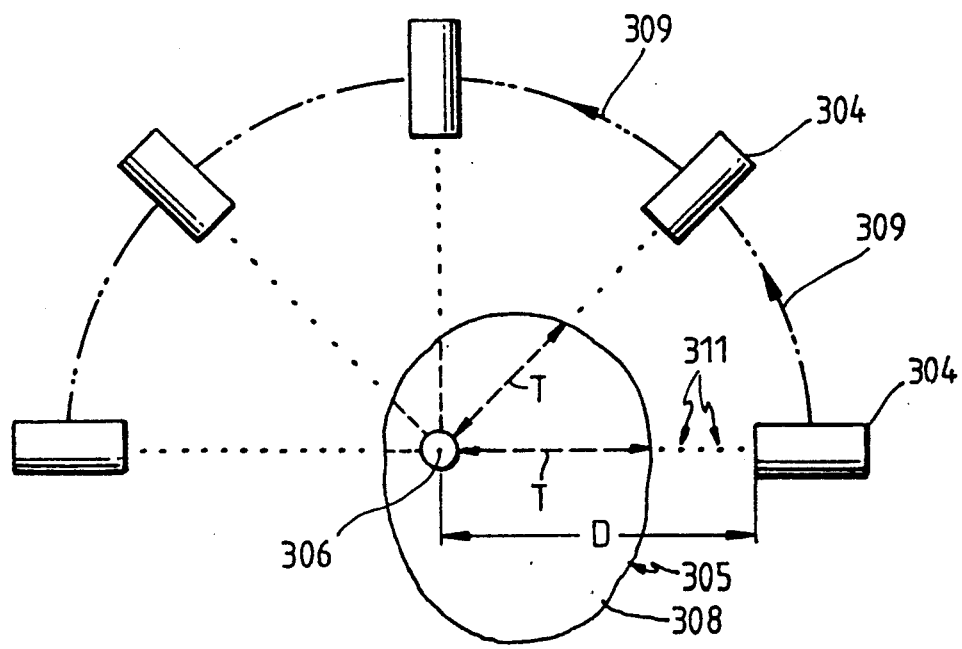
FIG. 2 is a top, schematic view of a patient's skull being treated with a conventional linear accelerator.

With reference to FIG. 2, the operation of linear accelerator 300 upon a lesion, or tumor, 306 in the skull 308 of patient 305 is illustrated. As collimator 304 is caused to rotate about the skull 308 of patient 305, along the path shown by dotted lines 309, a beam of radiation 311, made up of photons which generate gamma rays when they impinge on human tissue, is focused and directed toward target 306. Collimator 304 is of conventional construction and defines the size of the beam of radiation 311 exiting from the conventional accelerator head 312 (FIG. 1) of linear accelerator 300. Conventional collimators 304 are either removeable, rigid tubes which create either a square or circular beam of varying size, or contain configurable leaflets so that an irregularly shaped beam can be produced. The aperture size of collimator 304 are determined and selected in accordance with the size of lesion 306 to be treated. Conventional collimators are attached to the accelerator head 312 at a fixed distance from the isocenter 307 of the linear accelerator 300. Since the distance D from the end of the collimator 304 to the target 306 is a constant value, and since the depth T of the target 306 with respect to the surface of the skull 308 varies, as illustrated in FIG. 2, as accelerator head 312 (FIG. 1) and collimator 304 rotates, the amount of tissue which the beam of radiation 311 passes through after it leaves the end of the collimator 304 on its way to the target 306, varies as well. It is this variance in the depth of the tissue T passed through by the treatment beam of radiation 311 which necessitates the sophisticated treatment planning system previously described.

With reference now to FIG. 3, the method of stereotactic-guided radiation therapy and collimator 304' of the present invention will be described. The same reference numerals will be used for the same components previously described, and primed reference numerals will be used for similar components to those previously described. The patient 305 of FIG. 3 is as illustrated in FIG. 1, placed upon the rotatable couch 303 of linear accelerator 300, and the target, or lesion, 306 is disposed at the isocenter 307 of the linear accelerator 300 as previously described. Collimator 304' includes: a means for focusing 315 a beam of radiation 311, or a conventional collimator 304 previously described; and a means for providing 316 a variable length pathway 317 for the beam of radiation 311. The pathway 317 has a material 318 substantially equivalent to tissue of the patient 305 associated with the pathway 317, and the beam of radiation 311 passes through the variable length pathway 317 prior to entering the patient 305.

As illustrated in FIG. 3, the beam of radiation 311 is focused by collimator 304' toward the lesion 306 and through the variable length pathway 317 and through the tissue equivalent material 318 associated with variable length pathway 317. Collimator 304' is moved with respect to the patient 305 along path 309 while the beam of radiation 311 is focused toward the lesion 306. As collimator 304' is moved along path 309, the length L of the variable length pathway 317 is varied so that the beam of radiation 311 passes through substantially the same distance T of tissue of patient 305 and tissue equivalent material 318 while the collimator 304' is being moved with respect to the patient 305 along path 309.

As seen in FIG. 3, as collimator 304' is rotated about the skull 308 of patient 305 with lesion 306 disposed at the isocenter of linear accelerator 300, which is also the center of rotation of collimator 304', the distance D from a fixed point 320 on collimator 304' remains constant. As previously discussed, as collimator 304' rotates along path 309, the depth or thickness T of tissue through which radiation beam 311 passes varies, as previously described. As seen in FIG. 3, as collimator 304' rotates about path 309, the length L of variable length pathway 317 also varies. As collimator 304' rotates about path 309, the radiation beam 311 will always pass through substantially the same distance of tissue, or tissue depth T, and tissue equivalent material 318 associated with variable length pathway 317; the sum of the depth of tissue T and variable length L of tissue equivalent material 318 being substantially equal to the distance D between a fixed point 320 on collimator 304' and the target, or tumor, 306 of patient 305. Thus, the effective tissue target depth D remains the same, and regardless of the location of the target 306, the beam of radiation 311 will pass through that constant effective tissue target depth D comprised of actual tissue target depth T and the variable length L of tissue equivalent material 318. Thus, the amount of radiation focused toward lesion 306 as collimator 304' rotates about a skull 308 of patient 305 will always be a fixed constant determined by the physical characteristics of the collimator 304'.

Since the effective tissue target depth D is always the same, the isodense distribution around the target 306 becomes independent of the target tissue depth T. Accordingly, the previously required computer hardware and software intensive treatment planning, which utilizes a complicated three-dimensional algorithm, of prior art systems is eliminated. For a stereotactic-guided radiation therapy treatment consisting of a single rotation of the collimator 304' the isodense distribution around the target 306 will always be circular. For convergent or multiple arc rotational treatments, the isodense distribution of the radiation around the target 306 will be spherical, provided that enough treatment arcs are used to deliver the total radiation dosage. Irregularly shaped lesions 306 may be treated in a conventional manner by overlapping spherical fields.

Stereotactic-guided radiation therapy treatment planning, in accordance with the present invention, thus becomes dependent only upon: the size of the target, or tumor 306, which determines the aperture size of the conventional, rigid, beam defining collimator 304; the stereotactic coordinates of the target 306 which are used in placing the patient 305 on the rotatable couch 303 of linear accelerator 300 and disposing the patient's lesion 306 at the isocenter 307 of the linear accelerator 300; and the total planned radiation dosage and the stored characteristics of the radiation beam and collimator 304 employed, both of which are used in a conventional manner to adjust the unit settings on the linear accelerator 300. Factors related to the surface contours of the scalp, or skull 308, of patient 305 and the tissue target depth T, factors unique to any individual patient 305, are eliminated. The characteristics for the rigid collimator 304 will be predetermined and then becomes a constant for a given size collimator 304.

With reference now to FIGS. 4-10, an example is shown of how a patient's lesion, or tumor, 306 is disposed at the isocenter 307 of a linear accelerator 300. As will be hereinafter described in further detail, it should be noted that the method of stereotactic-guided radiation therapy, collimator 304' and system for stereotactic-guided radiation therapy of the present invention may be used not only for the treatment of lesions disposed within the skull 308 of a patient 305, but may also be utilized to treat lesions disposed in other parts of patient 305 wherever there is a relatively constant tissue density, which generally are those areas outside of the patient's thorax. Although when such other lesions, or tumors, 306 are treated, more normal tissue may be exposed to radiation when using a rotating collimator than in conventional stationary port plans, the exposure is so small that the benefits in terms of the steepness of the isodose curves are believed to far outweigh any potential liabilities.

As seen in FIG. 4, patient 305 had a lesion or tumor 306 disposed within his skull 308. With reference to FIGS. 5 and 6, a stereotactic fixation device 330 is shown to include a positioning fixture 331 which is secured to the patient's skull 308 in a suitable location with conventional bone screws (not shown). Positioning fixture 331 also includes a ball socket member 332 which is secured to the positioning fixture 331 prior to computerized tomographic ("CT") scanning of the patient. Stereotactic fixation device 330 may be any conventional stereotactic fixation device, so long as stereotactic fixation device 330 does not present collimator 304' with any significant obstructions as it moves along paths 309 as will be hereinafter described in greater detail. One such prior art stereotactic fixation device 330 which may be utilized in practicing the method of the present invention is that disclosed in U.S. Pat. No. 4,805,615, issued Feb. 21, 1989, to the inventor of the present invention, which patent is incorporated herein by reference.

With reference to FIGS. 7 and 8, the patient 305 is placed upon the CT imager table 333 of CT scanner 334, and the ball socket member 332 is fixedly attached to imager table 333 via an attachment member, or alignment rod, 335 and bracket 336. The ball socket member 332 allows the ball of the ball socket member 332 to swivel until the attachment member, or alignment rod, 335 can mate with the rod 337 attached to ball socket member 332. Once the alignment rod 335 and ball rod member 337 are mated, the ball of ball socket member 332 is locked in place and the patient 305 is imaged in the CT scanner 334 in a conventional manner, whereby the stereotactic coordinates of the target, or lesion, 306 are determined.

With reference to FIGS. 9 and 10, the patient is then transferred to the rotatable couch 303 of linear accelerator 300 where the ball rod 337 is connected to an alignment rod, or attachment member, 335 and bracket 336 which are identical to those associated with the CT scanner 334, whereby the geometric disposition of the patient with respect to rotatable couch 303 is a duplicate of the geometric relationship of the patient 305 with respect to the imaging table 333. The ball of ball socket member 332 is then brought to lie at the isocenter 307 of the linear accelerator 300 by moving the rotatable couch 303 in a conventional manner. The target, or lesion, 306 may then be brought to be disposed at the isocenter 307 of the linear accelerator 300 by adjusting the position of the rotatable table 303 in accordance with the stereotactic coordinates of the tumor 306 which were determined in the CT scanner 334. As seen in FIG. 10, with the tumor 306 being 300, collimator 304', including the means for providing 316 a variable length pathway 317 are rotated about patient 305 in the manner previously described in connection with FIG. 3. It should be noted that for treatment of lesions, or tumors, in other areas of the patient's body, other than skull 308, the previously described steps would be followed, with the exception that the positioning fixture 331 and ball socket member 332 of stereotactic fixation device 330 would not be disposed upon the skull 308 of patient 305, but would be disposed upon another portion of the patient's body, such as the sternum, as by an adhesive, whereby that portion of the body wherein the tumor 306 is disposed may be scanned by the CT scanner 334 in the manner previously described, the patient's orientation on the imaging table 333 being duplicated upon the rotatable couch 303 of linear accelerator 300, in the manner previously described.

With reference now to FIGS. 11-15, a collimator 304' in accordance with the present invention, useful in treating a patient with stereotactic-guided radiation therapy, includes means for focusing 315 a beam of radiation, or a conventional rigid tube collimator 304; and means for providing 316 a variable length pathway 317 for a beam of radiation, pathway 317 having a tissue equivalent material 318 associated therewith. As previously described, the tissue equivalent material 318 is preferably water, in that water has approximately the same energy dissipation or attenuation, properties as normal human tissue. As previously discussed, when a beam of radiation passes through human tissue, its energy is dissipated or attenuated. It should be noted that tissue equivalent material 318 could be any other material having substantially similar density and energy dissipation and attenuation characteristics as normal tissue. Alternatively, materials with density, energy dissipation and attenuation characteristics which vary linearly as a function of the thickness of the material may be used, whereby knowing the density, energy dissipation and attenuation characteristics of the material 318, it would be possible to callibrate collimator 304' to provide a known quantity of radiation energy to a lesion 306 (FIG. 3) dependent upon the thickness, or variable length L of material 318 through which the beam of radiation 311 travels when used in the method and apparatus previously described in connection with FIG. 3.

Still with reference to FIGS. 11-15, variable length pathway providing means 316 may include a variable length movable housing 340 which contains the tissue equivalent material 318. The variable length pathway providing means 316 may further include a reservoir 341 for the tissue equivalent material 318, the tissue equivalent material 318 being contained in reservoir 341 not having the beam of radiation pass therethrough. Collimator 304' preferably includes a base member 342, or circular flange 343 which permits the collimator 304' to be fixedly secured to the accelerator head 312 of linear accelerator 300 (FIG. 1). In the embodiment of collimator 304' of FIGS. 11-15, the variable length, movable housing 340 may be afforded by a cylinder 345 which is matingly received by another cylinder 346 in a fluid sealed relationship, the bottom of cylinder 345 having an anular flange plate 347 being disposed in a sealing relationship with respect to the interior of cylinder 346 and a central tube 348. The upper end of cylinder 345 is sealed by an end plate member 349. End plate member 349 may include at least two or more guide cylinders 350 which cooperate with guide rods 351 to properly align the mating cylinders 345, 346 of variable length, movable housing 340 as they move with respect to one another as will be hereinafter described. It should be noted that variable length, movable housing 340 could have any suitable configuration, such as the cylindrical configuration illustrated in FIGS. 11-15; however, any other suitable cross-sectional configuration could be utilized such as square, triangular, etc.

In the embodiment of collimator 304' illustrate in FIGS. 11-15, the mating portions 345, 346 of variable length, movable housing 340 are sized so that the volume of tissue equivalent material 318 contained between cylinders 345, 346, as illustrated in FIG. 11 is equal to the sum of the volume contained in cylinder 345 and the volume shown at the top of cylinder 346 in FIG. 13, so that when the variable length, movable housing 340 is in its fully extended position shown in FIG. 13, the cavity within cylinder 345 will be completely full of the tissue equivalent material, or water, 318. It should be noted that the top of cylinder 346 has an anular plate 352 secured thereto in a fluid tight relationship with the top of cylinder 346 and the outer wall surface of cylinder 345. Further, the lower end of cylinder 345 is in fluid communication with the interior of cylinder 346, as by a plurality of openings 353 formed in the lower wall surface of cylinder 345 above the anular sealing plate 347 of cylinder 345. Alignment rods 351 may have a plurality of bearings 355 disposed thereon to cooperate with the interior of alignment tubes 350.

Variable length, movable housing 340 has at its first end 360 or end plate 349, a means for controlling 361 the movement of the housing 340. Control means 361 may preferably be at least one sensor means 362, or conventional proximity switch, which operates to control the operation of a motor (not shown) which moves cylinder 345 upwardly or downwardly, to vary the length of the variable length pathway 317. The sensor means 361, or switch 362 may preferably be a pressure sensitive switch. Collimator 304' in the preferred embodiment of the method of stereotactic-guided radiation therapy in accordance with the present invention, includes the step of contacting the patient 305 (FIG. 3) with a first end 360, or end plate 349, of the variable length pathway 317, and maintaining such contact while the collimator 304' is being moved by varying the length L of the variable length pathway 317 or variable length, movable housing 340. Accordingly, sensor means 361, or switch 362 operates to control the motor (not shown), whereby the motor is operated to move the first end 360, or end plate 349 of variable length pathway 317, or variable length, movable housing 40, into contact with patient 305, as well as maintain such contact while collimator 304' is being moved along path 309 (FIG. 3) as previously described. Alternatively, the method of stereotactic-guided radiation therapy of the present invention includes the step of disposing the first end 360 of the variable length pathway 317 a predetermined distance from the patient 305 and maintaining that predetermined distance between the first end 360 and the patient 305 while the collimator 304' is moved by varying the length L of the variable length pathway 317 or variable length, movable housing 340. In that embodiment, sensor means 361, or switch 362, can be a location sensor switch or sonar type switch which detects the location of the skull 308, or other portion of the body, of patient 305 and controls the operation of the motor (not shown) to maintain a predetermined fixed distance between the end 360 variable length pathway 317, or variable length, movable housing 340 from the skull 308 or other portion of the body of patient 305.

With reference now to FIGS. 16-20, another embodiment 304" of collimator 304' is shown. For those components which are the same as those previously described in connection with FIGS. 11-15, the same reference numerals will be utilized, and for similar components primed reference numerals will be utilized. Collimator 304" includes a means for providing 316 a variable length pathway 317, wherein the variable length pathway providing means 316 includes a variable length, movable housing 340 having a first end 360, and contains the tissue equivalent material 318. A reservoir 341' for the tissue equivalent material is also provided. In the embodiment of collimator 304" of FIGS. 16 and 17, the variable length, movable housing 340 is a variable length, movable piston 380 which includes the tissue equivalent material 318. As piston 380 extends upwardly from the position shown in FIG. 16 to the fully extended position shown in FIG. 17, the tissue equivalent material is drawn upwardly from reservoir 341' through passageway 381 into the interior of piston 380, or variable length pathway 317. Variable length, movable housing 340 is provided with similar guide rods 351' and guide tubes 350, the guide tubes 350' having bearings 355 disposed therein, for aligning the movable housing 340 as it moves upwardly and downwardly.

Reservoir 341' may include a collapsible plastic enclosure 382, whereby upon the outward extension of piston 380, the plastic bag, or enclosure, 382 of reservoir 341' collapses as illustrated in FIG. 17. Piston 380 may preferably be formed of a spring 383 encased in a flexible plastic enclosure 384 thus forming a variable length, movable bellows 385, which permits the variable length, movable piston 380 to expand and contract as illustrated in FIGS. 16 and 17, and to additionally draw the tissue equivalent material 318 through passageway 381 in the manner previously described as bellows 385 expands into the position shown in FIG. 17. Collimator 304" may be provided with the same control means 361 as previously described, or alternatively, spring 383 may provide a means for spring biasing the first end 360 of the movable housing 340 into contact with patient 305. Thus, the force exerted by spring 383 upon the end plate 349' of housing 340 serves to keep end plate 349' in contact with the patient 305 as collimator 304" is moved about patient 305.

The embodiment 304''' of collimator 304' in FIG. 20 is identical to that illustrated in connection with FIGS. 16-19, with exception that collimator 304''' is provided with a motor 400 which controls the operation and movement of the variable length, movable housing 340. Collimator 304''' is provided with control means 361 or switch 362 which is operatively associated with motor 400, whereby motor 400 causes the movement of movable housing 340, as by a gear 401 contacting a mating gear disposed upon one of the guide rods 351'', whereby movable housing 340, or piston 380 may be raised or lowered as illustrated in FIGS. 16 and 17.

It is to be understood that the invention is not to be limited to the exact details of construction, operation, exact materials or embodiments shown and described, as obvious modifications and equivalents will be apparent to one skilled in the art; for example, other types of control means could be used to control the varying of the length of the variable length pathway. Accordingly, the invention is therefore to be limited only by the scope of the appended claims.

I claim:

1. A collimator useful in treating a patient with stereotactic-guided radiation therapy of a lesion within a patient's body comprising:
    means for focusing a beam of radiation; and
    means for providing a variable length pathway for the beam of radiation, the pathway having a material substantially equivalent to tissue of the patient associated with the pathway, the beam of radiation passing through the pathway prior to entering the patient, the length of the pathway throughout the therapy being varied to pass the beam of radiation through substantial the same distance of tissue and tissue equivalent material before the beam of radiation is delivered to the lesion, whereby the lesion is treated through the therapy with substantially the same amount of radiation.

2. The collimator of claim 1, wherein the tissue equivalent material is water.

3. The collimator of claim 1, wherein the variable length pathway providing means includes a variable length, movable housing which contains the tissue equivalent material.

4. The collimator of claim 3, wherein the tissue equivalent material is water.

5. The collimator of claim 3, wherein the variable length pathway providing means further includes a reservoir for the tissue equivalent material.

6. The collimator of claim 3, wherein the variable length, movable housing is a variable length, movable piston, and the piston contains the tissue equivalent material.

7. The collimator of claim 6, wherein the piston is a plastic encased spring which forms a variable length, movable bellows for containing the tissue equivalent material.

8. The collimator of claim 3, wherein the housing has a first end, adapted to contact the patient, and means for controlling the movement of the housing, whereby the first end of the housing maintains contact with the patient.

9. The collimator of claim 8, wherein the control means is a means for spring biasing the first end of the housing into contact with the patient.

10. The collimator of claim 8, wherein the control means is at least one sensor, means associated with the first end of the housing and a motor the at least one sensor means further controlling the operation of the motor which moves and maintains the housing in contact with the patient.

11. A system for stereotactic-guided radiation therapy for treating a lesion within a patient's body comprising:
    a stereotactic fixation device;
    a linear accelerator having a rotatable couch; and
    a collimator for focusing a beam of radiation from the linear accelerator, including means for providing a variable length pathway for the beam of radiation, the pathway having a material substantially equivalent to tissue of the patient associated with the pathway, the beam of radiation passing through the pathway prior to entering the patient, the length of the pathway throughout the therapy being varied to pass the beam of radiation through substantially the same distance of tissue and tissue equivalent material before the beam of radiation is delivered to the lesion, whereby the lesion is treated throughout the therapy with substantially the same amount of radiation.

12. The system of claim 11, wherein the tissue equivalent material is water.

13. The system of claim 11, wherein the variable length pathway providing means includes a variable length, movable housing which contains the tissue equivalent material.

14. The system of claim 13, wherein the tissue equivalent material is water.

15. The system of claim 13, wherein the variable length pathway providing means further includes a reservoir for the tissue equivalent material.

16. The system of claim 13, wherein the variable length, movable housing is a variable length, movable piston, and the piston contains the tissue equivalent material.

17. The system of claim 16, wherein the piston is a plastic encased spring which forms a variable length, movable bellows for containing the tissue equivalent material.

18. The system of claim 13, wherein the housing has a first end, adapted to contact the patient, and means for controlling the movement of the housing, whereby the first end of the housing maintains contact with the patient.

19. The system of claim 18, wherein the control means is a means for spring biasing the first end of the housing into contact with the patient.

20. The system of claim 18, wherein the control means is at least one sensor means associated with the first end of the housing and a motor, the at least one sensor means further controlling the operation of the motor which moves and maintains the housing in contact with the patient.

21. A method of stereotactic-guided radiation therapy of a lesion within a patient's body comprising the steps of:
    placing the patient on a rotatable couch associated with a linear accelerator having a collimator and a gantry;
    disposing the lesion of the patient at the isocenter of the linear accelerator;
    focusing a beam of radiation toward the lesion and through a variable length pathway associated with the collimator, the pathway having a material substantially equivalent to the tissue of the patient, the beam of radiation passing through the pathway prior to entering the patient;

moving the collimator with respect to the patient while focusing the beam of radiation toward the lesion; and varying the length of the variable length pathway while moving the collimator, so that the beam of radiation passes through substantially the same distance of tissue and tissue equivalent material while the collimator is being moved, and the lesion is treated throughout the therapy with substantially the same amount of radiation.

22. The method of claim 21, including the step of utilizing water as the tissue equivalent material.

23. The method of claim 21, including the step of contacting the patient with a first end of the variable length pathway and maintaining such contact while the collimator is being moved by varying the length of the variable length pathway.

24. The method of claim 21, including the step of disposing a first end of the variable length pathway a predetermined distance from the patient, and maintaining the predetermined distance between the first end and the patient while the collimator is moving by varying the length of the variable length pathway.

* * * * *

UNITED STATES PATENT AND TRADEMARK OFFICE
CERTIFICATE OF CORRECTION

PATENT NO. : 5,037,374

DATED : August 6, 1991

INVENTOR(S) : Mark P. Carol

It is certified that error appears in the above-identified patent and that said Letters Patent is hereby corrected as shown below:

In Column 11, line 31, "substantial" should read --substantially--.

In Column 11, line 64, delete "," after "sensor".

In Column 11, line 65, after "motor" insert --,--.

Signed and Sealed this

Twenty-ninth Day of December, 1992

Attest:

DOUGLAS B. COMER

*Attesting Officer*　　　*Acting Commissioner of Patents and Trademarks*